(12) United States Patent
Ansmann et al.

(10) Patent No.: US 6,235,702 B1
(45) Date of Patent: May 22, 2001

(54) AQUEOUS NACREOUS LUSTRE CONCENTRATE

(75) Inventors: Achim Ansmann, Erkrath; Rolf Kawa, Monheim; Stefan Podubrin, Muelheim; Alfred Westfechtel, Hilden, all of (DE)

(73) Assignee: Henkel Kommaditgesellschaft auf Aktien, Duesseldorf (DE)

( * ) Notice: Subject to any disclaimer, the term of this patent is extended or adjusted under 35 U.S.C. 154(b) by 0 days.

(21) Appl. No.: 09/194,410

(22) PCT Filed: May 22, 1997

(86) PCT No.: PCT/EP97/02617

§ 371 Date: Mar. 31, 1999

§ 102(e) Date: Mar. 31, 1999

(87) PCT Pub. No.: WO97/46209

PCT Pub. Date: Dec. 11, 1997

(30) Foreign Application Priority Data

May 30, 1996 (DE) .............................................. 196 21 681

(51) Int. Cl.⁷ .............................. C11C 3/08; C11C 1/825
(52) U.S. Cl. ......................... 510/416; 510/505; 510/506; 252/586; 560/180
(58) Field of Search .................................. 252/311, 312, 252/314, 610, 586; 510/130, 159, 416, 505, 506, 125, 122; 426/610; 424/70.1, 70.31; 560/180

(56) References Cited

U.S. PATENT DOCUMENTS

| | | | |
|---|---|---|---|
| 3,547,828 | 12/1970 | Mansfield et al. | 252/351 |
| 3,707,535 | 12/1972 | Lew | 260/210 R |
| 3,772,269 | 11/1973 | Lew | 260/210 R |
| 3,839,318 | 10/1974 | Mansfield | 260/210 R |
| 4,078,147 | * 3/1978 | Ukai et al. | 560/180 |
| 4,172,887 | 10/1979 | Vanlerberghe et al. | 424/70 |
| 4,349,669 | 9/1982 | Klahr et al. | 536/127 |
| 4,438,096 | 3/1984 | Preston | 424/70 |
| 4,777,038 | 10/1988 | Scheuffgen | 424/70 |
| 5,403,508 | 4/1995 | Reng et al. | 252/174.22 |
| 5,711,899 | 1/1998 | Kawa et al. | 252/311 |

FOREIGN PATENT DOCUMENTS

| | | | |
|---|---|---|---|
| 11 65 574 | 3/1964 | (DE) . | |
| 1165574 | * 3/1964 | (DE) | 120/11 |
| 19 43 689 | 3/1970 | (DE) . | |
| 20 36 472 | 2/1971 | (DE) . | |
| 30 01 064 | 7/1981 | (DE) . | |
| 20 24 051 | 5/1986 | (DE) . | |
| 38 43 572 | 6/1990 | (DE) . | |
| 41 03 551 | 8/1992 | (DE) . | |
| 0 077 167 | 4/1983 | (EP) . | |
| 0 181 773 | 5/1986 | (EP) . | |
| 0 285 389 | 10/1988 | (EP) . | |
| 0 205 922 | 8/1992 | (EP) . | |
| 0 569 843 | 11/1993 | (EP) . | |
| 0 684 302 | 11/1995 | (EP) . | |
| 0 581 193 | 6/1998 | (EP) . | |
| 2 252 840 | 12/1978 | (FR) . | |
| 962 919 | 7/1964 | (GB) . | |
| 1333475 | 10/1973 | (GB) . | |
| 57-067510 | 4/1982 | (JP) . | |
| 7-082140 | 3/1995 | (JP) . | |

OTHER PUBLICATIONS

Chemical Abstract 208463, vol. 123, No. 16, Oct. 16, 1995.
Chemical Abstract 60813, vol. 97, No. 8, Aug. 23, 1982.
Ansmann, et al., Parfuemerie und Kosmetik, vol. 75, (Sep. 1994) pp. 578–580.
J. Falbe (ed.), "Surfactants in Consumer Products", Springer Verlag, Berlin, (1987), pp. 54–124.
J. Falbe (ed.), "Katalysatoren, Tenside und Mineraloeladditive", Thieme Verlag, Stuttgart, (1978), pp. 123–217.
"Kosmetische Faerbemittal", Farbstoffkommission der Deutschen Forschungsgemeinschaft, Verlag Chemie, Weinheim, (1984) pp. 81–106.

* cited by examiner

Primary Examiner—Yogendra Gupta
Assistant Examiner—Gregory E. Webb
(74) Attorney, Agent, or Firm—John E. Drach; Steven J. Trzaska

(57) ABSTRACT

A concentrated aqueous pearlescent composition containing: (a) from 1 to 99.9% by weight of an ester formed by reacting a hydroxy-functionalized carboxylic acid with a fatty alcohol containing from 6 to 22 carbon atoms; (b) from 0.1 to 90% by weight of an emulsifier selected from the group consisting of an anionic surfactant, a nonionic surfactant, a cationic surfactant, an ampholytic surfactant, a zwitterionic surfactant, an esterquat, and mixtures thereof; and (c) up to 40% by weight of a polyol, all weights being based on the total weight of the composition.

19 Claims, No Drawings

AQUEOUS NACREOUS LUSTRE CONCENTRATE

BACKGROUND OF THE INVENTION

1. Field of the Invention

This invention relates to aqueous pearlescent concentrates containing esters of polybasic carboxylic acids or hydroxycarboxylic acids, emulsifiers and optionally polyols, to a process for their production, to a process for the production of pearlescent surface-active formulations using the concentrates and to the use of esters of polybasic carboxylic acids and hydroxycarboxylic acids as pearlescent waxes.

2. Discussion of Related Art

For centuries, the softly shimmering luster of pearls has held a particular fascination for human beings. It is therefore no wonder that manufacturers of cosmetic preparations endeavour to give their products an attractive, valuable and rich appearance. The first pearlescence used in cosmetics in the middle ages was a pearlescent paste of natural fish scales. At the beginning of the present century, it was discovered that bismuth oxide chlorides were also capable of producing pearlescence. By contrast, pearlescent waxes, particularly of the glycol monofatty acid ester and difatty acid ester type, are of importance in modem cosmetics, being used mainly for the production of pearlescence in hair shampoos and shower gels. An overview of modern pearlescent formulations was published by A. Ansmann and R. Kawa in Parf. Kosm., 75, 578 (1994).

Various formulations capable of providing surface-active products with the required pearlescence are known from the prior art. For example, German patent applications DE-A1 38 43 572 and DE-A1 41 03 551 (Henkel) describe pearlescent concentrates in the form of free-flowing aqueous dispersions containing 15 to 40% by weight of pearlescent components, 5 to 55% by weight of emulsifiers and 0.1 to 5% by weight or 15 to 40% by weight of polyols. The pearlescent waxes are acylated polyalkylene glycols, monoalkanolamides, linear saturated fatty acids or ketosulfones. European patents EP-B1 0 181 773 and EP-B1 0 285 389 (Procter & Gamble) describe shampoo compositions containing surfactants, non-volatile silicones and pearlescence waxes. European patent application EP-A2 0 205 922 (Henkel) relates to free-flowing pearlescent concentrates containing 5 to 15% by weight of acylated polyglycols, 1 to 6% by weight of fatty acid monoethanolamides and 1 to 5% by weight of nonionic emulsifiers. According to the teaching of European patent EP-B1 0 569 843 (Hoechst), nonionic, free-flowing pearlescent dispersions can also be obtained by preparing mixtures of 5 to 30% by weight of acylated polyglycols and 0.1 to 20% by weight of selected nonionic surfactants. In addition, European patent application EP-A2 0 581 193 (Hoechst) describes free-flowing, preservative-free pearlescent dispersions containing acylated polyglycol ethers, betaines, anionic surfactants and glycerol. Finally, European patent application EP-A1 0 684 302 (Th. Goldschmidt) relates to the use of polyglycerol esters as crystallization aids for the production of pearlescent concentrates.

Despite the large number of formulations, there is a constant need on the market for new pearlescent waxes which, in contrast to acylated polyglycols for example, do not contain any ethylene oxide units and which are distinguished from known products by their brilliant luster, even when used in smaller quantities, so that critical ingredients, such as silicones for example, may also be used without any adverse effect on the stability of the formulations and which, at the same time, contain ester groups, thus guaranteeing adequate biodegradability, and which are free-flowing and hence easy to handle, particularly in concentrated form. Accordingly, the problem addressed by the present invention was to provide new pearlescent concentrates which would satisfy the complex requirement profile described above.

DESCRIPTION OF THE INVENTION

The present invention relates to aqueous pearlescent concentrates containing—based on the non-aqueous component (a) 1 to 99.1 % by weight of esters of polybasic and optionally hydroxy-functionalized carboxylic acids with fatty alcohols containing 6 to 22 carbon atoms, (b) 0.1 to 90% by weight of anionic, nonionic, cationic, ampholytic and/or zwitterionic emulsifiers and (c) 0 to 40% by weight of polyols, with the proviso that the quantities add up to 100% by weight.

It has surprisingly been found that esters of polybasic carboxylic and/or hydroxycarboxylic acids with fatty alcohols have excellent pearlescing properties and are distinguished from known products by greater brilliance, even when used in smaller quantities, particular particle fineness and stability in storage. The pearlescent waxes are readily biodegradable and free-flowing in concentrated form and even enable problematical ingredients, for example silicones, to be incorporated in cosmetic formulations.

Polybasic Carboxylic Acid and Hydroxycarboxylic Acid Esters

The pearlescent waxes which form component (a) are known substances which may be obtained by the relevant methods of preparative organic chemistry. The esters are normally prepared in known manner by base-catalyzed esterification of carboxylic acids and/or hydroxycarboxylic acids containing 4 to 12 carbon atoms, 2 to 4 carboxyl groups and 1 to 5 hydroxyl groups with the fatty alcohols. Suitable acid components are, for example, malonic acid, maleic acid, fumaric acid, adipic acid, sebacic acid, azelaic acid, dodecanedioic acid, phthalic acid, isophthalic acid and, in particular, succinic acid and also malic acid, citric acid and, in particular, tartaric acid and mixtures thereof. The fatty alcohols contain 6 to 22, preferably 12 to 18 and, more preferably, 16 to 18 carbon atoms in the alkyl chain. Typical examples are caproic alcohol, caprylic alcohol, 2-ethylhexyl alcohol, capric alcohol, lauryl alcohol, isotridecyl alcohol, myristyl alcohol, cetyl alcohol, palmitoleyl alcohol, stearyl alcohol, isostearyl alcohol, oleyl alcohol, elaidyl alcohol, petroselinyl alcohol, linolyl alcohol, linolenyl alcohol, elaeostearyl alcohol, arachyl alcohol, gadoleyl alcohol, behenyl alcohol, erucyl alcohol and brassidyl alcohol and technical mixtures thereof. The esters may be present as full or partial esters, monoesters and above all diesters of the carboxylic or hydroxycarboxylic acids preferably being used. Typical examples are succinic acid mono- and dilauryl ester, succinic acid mono- and dicetearyl ester, succinic acid mono- and distearyl ester, tartaric acid mono- and dilauryl ester, tartaric acid mono- and dicocoalkyl ester, tartaric acid mono- and dicetearyl ester, citric acid mono-, di- and trilauryl ester, citric acid mono-, di- and tricocoalkyl ester and citric acid mono-, di- and tricetearyl ester. The esters may be used in quantities of 1 to 99.9% by weight, based on the concentrates, and are normally used in quantities of 5 to 75% by weight, preferably 10 to 50% by weight and more preferably 15 to 30% by weight.

Emulsifiers

The pearlescent concentrates according to the invention may contain nonionic surfactants from at least one of the following groups as emulsifiers:

(b1) adducts of 2 to 30 moles of ethylene oxide and/or 0 to 5 moles of propylene oxide with linear fatty alcohols containing 8 to 22 carbon atoms, with fatty acids containing 12 to 22 carbon atoms and with alkylphenols containing 8 to 15 carbon atoms in the alkyl group;

(b2) $C_{12/18}$ fatty acid monoesters and diesters of adducts of 1 to 30 moles of ethylene oxide with glycerol;

(b3) glycerol monoesters and diesters and sorbitan monoesters and diesters of saturated and unsaturated fatty acids containing 6 to 22 carbon atoms and ethylene oxide adducts thereof;

(b4) alkyl mono- and oligoglycosides containing 8 to 22 carbon atoms in the alkyl group and ethoxylated analogs thereof;

(b5) adducts of 15 to 60 moles of ethylene oxide with castor oil and/or hydrogenated castor oil;

(b6) polyol esters and, in particular, polyglycerol esters such as, for example, polyglycerol polyricinoleate or polyglycerol poly-12-hydroxystearate. Mixtures of compounds from several of these classes are also suitable;

(b7) adducts of 2 to 15 moles of ethylene oxide with castor oil and/or hydrogenated castor oil;

(b8) partial esters based on linear, branched, unsaturated or saturated $C_{12/22}$ fatty acids, ricinoleic acid and 12-hydroxystearic acid and glycerol, polyglycerol, pentaerythritol, dipentaerythritol, sugar alcohols (for example sorbitol) and polyglucosides (for example cellulose);

(b9) trialkyl phosphates;

(b10) wool wax alcohols;

(b11) polysiloxane/polyalkyl polyether copolymers and corresponding derivatives;

(b12) mixed esters of pentaerythritol, fatty acids, citric acid and fatty alcohol according to DE-PS 11 65 574 and (b13) polyalkylene glycols.

The addition products of ethylene oxide and/or propylene oxide with fatty alcohols, fatty acids, alkylphenols, glycerol monoesters and diesters and sorbitan monoesters and diesters of fatty acids or with castor oil are known commercially available products. They are homolog mixtures of which the average degree of alkoxylation corresponds to the ratio between the quantities of ethylene oxide and/or propylene oxide and substrate with which the addition reaction is carried out. $C_{12/18}$ fatty acid monoesters and diesters of adducts of ethylene oxide with glycerol are known as refatting agents for cosmetic formulations from DE-PS 20 24 051.

$C_{8/18}$ alkyl mono- and oligoglycosides, their production and their use as surfactants are known, for example, from U.S. Pat. Nos. 3,839,318, 3,707,535, 3,547,828, DE-OS 19 43 689, DE-OS 20 36 472 and DE-A1 30 01 064 and also from EP-A 0 077 167. They are produced in particular by reacting glucose or oligosaccharides with primary $C_{8/18}$ alcohols. So far as the glycoside unit is concerned, both monoglycosides in which a cyclic sugar unit is attached to the fatty alcohol by a glycoside bond and oligomeric glycosides with a degree of oligomerization of preferably up to about 8 are suitable. The degree of oligomerization is a statistical mean value on which the homolog distribution typical of such technical products is based.

In addition, zwitterionic surfactants may be used as emulsifiers. Zwitterionic surfactants are surface-active compounds which contain at least one quaternary ammonium group and at least one carboxylate and one sulfonate group in the molecule. Particularly suitable zwitterionic surfactants are the so-called betaines, such as the N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known under the CTFA name of Cocoamidopropyl Betaine is particularly preferred. Ampholytic surfactants are also suitable emulsifiers. Ampholytic surfactants are surface-active compounds which, in addition to a $C_{8/18}$ alkyl or acyl group, contain at least one free amino group and at least one —COOH— or —SO$_3$H— group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-cocoalkylaminopropionate, cocoacylaminoethyl aminopropionate and $C_{12/18}$ acyl sarcosine. Besides ampholytic emulsifiers, quaternary emulsifiers may also be used, those of the esterquat type, especially methyl-quaternized difatty acid triethanolamine ester salts, being particularly preferred.

The pearlescent concentrates according to the invention may contain the emulsifiers in quantities of 0.1 to 90% by weight, preferably in quantities of 5 to 50% by weight and, more preferably, in quantities of 10 to 40% by weight.

Polyols

Polyols which may be used as component (c) in accordance with the invention preferably contain 2 to 15 carbon atoms and at least two hydroxyl groups. Typical examples are glycerol;

alkylene glycols such as, for example, ethylene glycol, diethylene glycol, propylene glycol, butylene glycol, hexylene glycol and polyethylene glycols with an average molecular weight of 100 to 1,000 dalton;

technical oligoglycerol mixtures with a degree of self-condensation of 1.5 to 10 such as, for example, technical diglycerol mixtures with a diglycerol content of 40 to 50% by weight;

methylol compounds such as, in particular, trimethylol ethane, trimethylol propane, trimethylol butane, pentaerythritol and dipentaerythritol;

lower alkyl glucosides, particularly those containing 1 to 8 carbon atoms in the alkyl group, for example methyl and butyl glucoside;

sugar alcohols containing 5 to 12 carbon atoms, for example sorbitol or mannitol, sugars containing 5 to 12 carbon atoms, for example glucose or sucrose;

aminosugars, for example glucamine.

The pearlescent concentrates according to the invention may contain the polyols, preferably glycerol, propylene glycol, butylene glycol, hexylene glycol and polyethylene glycols with an average molecular weight of 100 to 1,000 in quantities of 0.1 to 40% by weight, preferably in quantities of 0.5 to 15% by weight and, more preferably, in quantities of 1 to 5% by weight.

Production Process

In one preferred embodiment, which is also a subject of the invention, the pearlescent concentrates are produced by preparing a mixture of components (a), (b) and (c), heating it to a temperature 1 to 30° C. above the melting point of the mixture, mixing it with the necessary quantity of water having substantially the same temperature and then cooling the mixture to room temperature. In an alternative method of production, a concentrated aqueous (anionic) surfactant paste may be initially introduced, the pearlescent wax stirred in while heating and the mixture subsequently diluted with more water to the required concentration or the mixing step may be carried out in the presence of polymeric hydrophilic thickeners such as, for example, hydroxypropyl celluloses, xanthan gum or polymers of the carbomer type.

Commercial Applications

The pearlescent concentrates according to the invention are suitable for opacifying surface-active formulations such as, for example, hair shampoos or manual dishwashing detergents. Accordingly, the present invention also relates to a process for the production of opacified and pearlescent liquid aqueous preparations of water-soluble surface-active substances, in which the pearlescent concentrates are added to the clear aqueous preparations at 0 to 40° C. in a quantity of 0.5 to 40% by weight and preferably 1 to 20% by weight of the preparation and are dispersed therein by stirring.

Surfactants

The surface-active formulations according to the invention, which have a non-aqueous component of generally 1 to 50 and preferably 5 to 35% by weight, may contain nonionic, anionic, cationic and/or amphoteric or zwitterionic surfactants which may be present in the formulations in quantities of normally about 50 to 99% by weight and preferably 70 to 90% by weight. Typical examples of anionic surfactants are soaps, alkyl benzenesulfonates, alkanesulfonates, olefin sulfonates, alkylether sulfonates, glycerol ether sulfonates, α-methyl ester sulfonates, sulfo-fatty acids, alkyl sulfates, fatty alcohol ether sulfates, glycerol ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids such as, for example, acyl lactylates, acyl tartrates, acyl glutamates and acyl aspartates, alkyl oligoglucoside sulfates, protein fatty acid condensates (particularly wheat-based vegetable products) and alkyl (ether) phosphates. If the anionic surfactants contain polyglycol ether chains, they may have a conventional homolog distribution although they preferably have a narrow-range homolog distribution. Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers and mixed formals, alk(en)yl oligoglycosides, fatty acid N-alkyl glucamides, protein hydrolyzates (particularly wheat-based vegetable products), polyol fatty acid esters, sugar esters, sorbitan esters, polysorbates and amine oxides. If the nonionic surfactants contain polyglycol ether chains, they may have a conventional homolog distribution, although they preferably have a narrow-range homolog distribution. Typical examples of cationic surfactants are quaternary ammonium compounds and esterquats, more particularly quaternized fatty acid trialkanolamine ester salts. Typical examples of amphoteric or zwitterionic surfactants are alkylbetaines, alkylamidobetaines, aminopropionates, aminoglycinates, imidazolinium betaines and sulfobetaines. The surfactants mentioned are all known compounds. Information on their structure and production can be found in relevant synoptic works, cf. for example J. Falbe (ed.), "Surfactants in Consumer Products", Springer Verlag, Berlin, 1987, pages 54 to 124 or J. Falbe (ed.), "Katalysatoren, Tenside und Mineralöladditive (Catalysts, Surfactants and Mineral Oil Additives)", Thieme Verlag, Stuttgart, 1978, pages 123–217. The same surfactants may also be directly used for the production of the pearlescent concentrates.

Auxiliaries and Additives

The surface-active formulations to which the pearlescent concentrates according to the invention may be added may contain other auxiliaries and additives such as, for example, oils, superfatting agents, stabilizers, waxes, consistency regulators, thickeners, cationic polymers, silicone compounds, biogenic agents, anti-dandruff agents, film-formers, preservatives, hydrotropes, solubilizers, UV absorbers, dyes and fragrances.

Suitable oils are, for example, Guerbet alcohols based on fatty alcohols containing 6 to 18 and preferably 8 to 10 carbon atoms, esters of linear $C_{6-20}$ fatty acids with linear $C_{6-20}$ fatty alcohols, esters of branched $C_{6-13}$ carboxylic acids with linear $C_{6-20}$ fatty alcohols, esters of linear $C_{6-18}$ fatty acids with branched alcohols, more particularly 2-ethyl hexanol, esters of linear and/or branched fatty acids with polyhydric alcohols (for example dimer diol or trimer diol) and/or Guerbet alcohols, triglycerides based on $C_{6-10}$ fatty acids, vegetable oils, branched primary alcohols, substituted cyclohexanes, Guerbet carbonates, dialkyl ethers and/or aliphatic or naphthenic hydrocarbons.

Superfatting agents may be selected from such substances as, for example, lanolin and lecithin and also polyethoxylated or acylated lanolin and lecithin derivatives, polyol fatty acid esters, monoglycerides and fatty acid alkanolamides, the fatty acid alkanolamides also serving as foam stabilizers. The consistency regulators mainly used are fatty alcohols containing 12 to 22 and preferably 16 to 18 carbon atoms. A combination of these substances with alkyl oligoglucosides and/or fatty acid N-methyl glucamides of the same chain length and/or polyglycerol poly-12-hydroxystearates is preferably used. Suitable thickeners are, for example, polysaccharides, more especially xanthan gum, guar-guar, agar-agar, alginates and tyloses, carboxymethyl cellulose and hydroxyethyl cellulose, also relatively high molecular weight polyethylene glycol monoesters and diesters of fatty acids, polyacrylates, polyvinyl alcohol and polyvinyl pyrrolidone, surfactants such as, for example, ethoxylated fatty acid glycerides, esters of fatty acids with polyols, for example pentaerythritol or trimethylol propane, narrow-range fatty alcohol ethoxylates or alkyl oligoglucosides and electrolytes, such as sodium chloride and ammonium chloride.

Suitable cationic polymers are, for example, cationic cellulose derivatives, cationic starch, copolymers of diallyl ammonium salts and acrylamides, quaternized vinyl pyrrolidone/vinyl imidazole polymers such as, for example, Luviquat® (BASF AG, Ludwigshafen, FRG), condensation products of polyglycols and amines, quaternized collagen polypeptides such as, for example, Lauryldimonium Hydroxypropyl Hydrolyzed Collagen (Lamequat®L, Grünau GmbH), quaternized wheat polypeptides, polyethyleneimine, cationic silicone polymers such as, for example, Amidomethicone or Dow Corning, Dow Corning Co., USA, copolymers of adipic acid and dimethylaminohydroxypropyl diethylenetriamine (Cartaretine®, Sandoz AG, CH), polyaminopolyamides as described, for example, in FR-A 2 252 840 and crosslinked water-soluble polymers thereof, cationic chitin derivatives such as, for example, quaternized chitosan, optionally in microcrystalline distribution, condensation products of dihaloalkyls, for example dibromobutane, with bis-dialkylamines, for example, bis-dimethylamino-1,3-propane, cationic guar gum such as, for example, Jaguar®CBS, Jaguar®C-17, Jaguar®C-16 of Celanese, USA, quaternized ammonium salt polymers such as, for example, Mirapol® A-15, Mirapol® AD-1, Mirapol® AZ-1 of Miranol, USA.

Suitable silicone compounds are, for example, dimethyl polysiloxanes, methylphenyl polysiloxanes, cyclic silicones and amino-, fatty acid-, alcohol-, polyether-, epoxy-, fluorine- and/or alkyl-modified silicone compounds which may be both liquid and resin-like at room temperature. Typical examples of fats are glycerides while suitable waxes are inter alia beeswax, paraffin wax or microwaxes, optionally in combination with hydrophilic waxes, for example cetyl stearyl alcohol. Besides the hydroxycarboxylic acid esters, other known pearlescent waxes such as, in particular, mono- and difatty acid esters of polyalkylene glycols or partial glycerides may also be used for the purposes of the invention. Metal salts of fatty acids such as, for example, magnesium, aluminium and/or zinc stearate may be used as stabilizers. In the context of the invention, biogenic agents are, for example, bisabolol, allantoin, phytantriol, panthenol, AHA acids, plant extracts and vitamin complexes. Climbazol, octopirox and zinc pyrethion may be used as antidandruff agents. Typical film formers are, for example, chitosan, microcrystalline chitosan, quaternized chitosan, polyvinyl pyrrolidone, vinyl pyrrolidone/vinyl acetate copolymers, polymers of the acrylic acid series, quaternary cellulose derivatives, collagen, hyaluronic acid and salts thereof and similar compounds. In addition, hydrotropes such as, for example, ethanol, isopropyl alcohol, propylene glycol or glucose may be used to improve flow behavior. Suitable preservatives are, for example, phenoxyethanol, formaldehyde solution, parabens, pentanediol or sorbic acid. The dyes used may be selected from any of the substances which are permitted and suitable for cosmetic purposes, as listed for example in the publication "Kosmetische Färbemittel" of the Farbstoffkommission der Deutschen Forschungsgemeinschaft, published by Verlag Chemie, Weinheim, 1984, pages 81–106. These dyes are typically used in concentrations of 0.001 to 0.1% by weight, based on the mixture as a whole.

The total content of auxiliaries and additives may be from 1 to 50% by weight and is preferably from 5 to 40% by weight, based on the formulation. The formulations may be produced by standard cold or hot processes and are preferably produced by the phase inversion temperature method.

Finally, the present invention relates to the use of esters of polybasic, optionally hydroxysubstituted carboxylic acids with fatty alcohols containing 6 to 22 carbon atoms as pearlescent waxes for the production of surface-active formulations.

EXAMPLES

Pearlescent concentrates R1 to R6 according to the invention and comparison mixture R7 were stored for 14 days at 40° C., after which their viscosities were measured by the Brookfield method using an RVT viscosimeter (23° C., 10 r.p.m., spindle 5). Water-containing hair shampoos each containing 2 g of pearlescent concentrates R1 to R7, 15 g of coconut fatty alcohol+2 EO sulfate sodium salt, 3 g of dimethyl polysiloxane, 5 g of cocoalkyl glucoside and 1.5 g of an esterquat (water to 100% by weight) were then prepared by mixing the ingredients at 50° C. The particle fineness of the pearlescent crystals in the shampoos was visually evaluated under a microscope on a scale of 1=very fine crystals to 5=coarse crystals. Pearlescence was also evaluated on a scale of 1=brilliant to 5=dull. Opacity was visually determined and was evaluated as (+)=opaque or (−)=non-opaque. The compositions and results are set out in Table 1 where all quantities are expressed as percentages by weight.

TABLE 1

Composition and Performance of Pearlescent Concentrates

| Composition | R1 | R2 | R3 | R4 | R5 | R6 | R7 |
|---|---|---|---|---|---|---|---|
| Tartaric acid monocetearyl ester | 25 | — | 20 | 20 | — | — | — |
| Citric acid dicocoalkyl ester | — | 25 | — | — | — | — | — |
| Succinic acid dicetearyl ester | — | — | — | — | 25 | — | — |
| Succinic acid distearyl ester | — | — | — | — | — | 25 | — |
| Ethylene glycol distearate | — | — | 5 | 5 | — | — | 25 |
| Cocoalcohol + 4EO | 5 | 5 | 5 | — | 5 | 5 | 5 |
| Cocoalkyl glucoside | 9 | 9 | 9 | 15 | 9 | 9 | 9 |
| Coconut fatty acid betaine | 5 | 5 | 5 | 4 | 5 | 5 | 5 |
| Glycerol | 5 | 5 | 5 | 5 | 5 | 5 | 5 |
| Water | | | | To 100 | | | |
| Viscosity of the concentrates [mPas] | | | | | | | |
| After 1 d, 40° C. | 8,000 | 8,000 | 8,000 | 8,000 | 8,000 | 8,000 | 9,500 |
| After 14 d, 40° C. | 7,500 | 7,400 | 5,000 | 7,800 | 7,800 | 7,700 | 7,200 |
| Pearlescence in the formulation | | | | | | | |
| Luster | 1.5 | 1.5 | 1.0 | 1.5 | 1.5 | 1.5 | 2.0 |
| Particle fineness | 1.5 | 1.5 | 1.5 | 2.0 | 1.5 | 1.0 | 3.0 |
| Opacity | − | − | − | − | − | − | + |

What is claimed is:

1. A concentrated aqueous pearlescent composition comprising:
   (a) from 5 to 75% by weight of an ester formed by reacting a hydroxy-functionalized carboxylic acid with a fatty alcohol containing from 6 to 22 carbon atoms;
   (b) from 0.1 to 90% by weight of an emulsifier selected from the group consisting of an anionic surfactant, a nonionic surfactant, a cationic surfactant, an ampholytic surfactant, a zwitterionic surfactant, an esterquat, and mixtures thereof; and
   (c) up to 40% by weight of a polyol, all weights being based on the total weight of the composition.

2. The composition of claim 1 wherein the hydroxy-functionalized carboxylic acid contains from 4 to 12 carbon atoms, from 2 to 4 carboxyl groups, and from 1 to 5 hydroxyl groups.

3. The composition of claim 1 wherein the hydroxy-functionalized carboxylic acid is selected from the group consisting of tartaric acid, malic acid, citric acid, succinic acid, and mixtures thereof.

4. The composition of claim 1 wherein the fatty alcohol contains from 12 to 18 carbon atoms.

5. The composition of claim 1 wherein the ester is a diester of the hydroxy-functionalized carboxylic acid.

6. The composition of claim 1 wherein the emulsifier is a nonionic surfactant.

7. The composition of claim 1 wherein the emulsifier is present in the composition in an amount of from 5 to 50% by weight, based on the weight of the composition.

8. The composition of claim 1 wherein the polyol contains from 2 to 15 carbon atoms and at least two hydroxyl groups.

9. The composition of claim 1 wherein the polyol is present in the composition in an amount of from 0.5 to 15% by weight, based on the weight of the composition.

10. A water-soluble surface-active composition containing from 0.5 to 40% by weight of the concentrated aqueous pearlescent composition of claim 1.

11. A process for making a pearlescent concentrate composition comprising:
    (a) providing from 1 to 99.9% by weight of an ester formed by reacting a hydroxy-functionalized carboxylic acid with a fatty alcohol containing from 6 to 22 carbon atoms;
    (b) providing from 0.1 to 90% by weight of an emulsifier selected from the group consisting of an anionic surfactant, a nonionic surfactant, a cationic surfactant, an ampholytic surfactant, a zwitterionic surfactant, an esterquat, and mixtures thereof;
    (c) providing up to 40% by weight of a polyol, all weights being based on the total weight of the composition;
    (d) mixing (a)–(c) to form a pearlescent concentrate mixture;
    (e) heating the mixture to a temperature of from 1 to 30° C. above a melting point of the mixture;
    (f) adding an effective amount of water having substantially the same temperature as the mixture, to the mixture; and
    (g) cooling the mixture to room temperature.

12. The process of claim 11 wherein the hydroxy-functionalized carboxylic acid contains from 4 to 12 carbon atoms, from 2 to 4 carboxyl groups, and from 1 to 5 hydroxyl groups.

13. The process of claim 11 wherein the hydroxy-functionalized carboxylic acid is selected from the group consisting of tartaric acid, malic acid, citric acid, succinic acid, and mixtures thereof.

14. The process of claim 11 wherein the fatty alcohol contains from 12 to 18 carbon atoms.

15. The process of claim 11 wherein the ester is present in the composition in an amount of from 5 to 75% by weight, based on the weight of the composition.

16. The process of claim 11 wherein the emulsifier is a nonionic surfactant.

17. The process of claim 11 wherein the emulsifier is present in the composition in an amount of from 5 to 50% by weight, based on the weight of the composition.

18. The process of claim 11 wherein the polyol contains from 2 to 15 carbon atoms and at least two hydroxyl groups.

19. The process of claim 11 wherein the polyol is present in the composition in an amount of from 0.5 to 15% by weight, based on the weight of the composition.

* * * * *